(12) United States Patent
Ertel

(10) Patent No.: US 10,726,564 B2
(45) Date of Patent: Jul. 28, 2020

(54) ESTABLISHING AN OVERLAY IMAGE TO BE DISPLAYED FROM A BASE IMAGE DATASET AND A MODIFICATION IMAGE DATASET OF MEDICAL IMAGE DATASETS

(71) Applicant: Dirk Ertel, Forchheim (DE)

(72) Inventor: Dirk Ertel, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 287 days.

(21) Appl. No.: 15/788,904

(22) Filed: Oct. 20, 2017

(65) Prior Publication Data

US 2018/0122088 A1  May 3, 2018

(30) Foreign Application Priority Data

Oct. 27, 2016 (DE) .................. 10 2016 221 220

(51) Int. Cl.
*G06T 7/33* (2017.01)
*G06T 5/50* (2006.01)
*A61B 34/20* (2016.01)
*A61B 90/00* (2016.01)
*G06T 5/00* (2006.01)
(Continued)

(52) U.S. Cl.
CPC ............ *G06T 7/33* (2017.01); *A61B 34/20* (2016.02); *A61B 90/37* (2016.02); *G06T 5/002* (2013.01); *G06T 5/008* (2013.01); *G06T 5/20* (2013.01); *G06T 5/50* (2013.01); *G06T 7/0012* (2013.01); *A61B 2034/2065* (2016.02); *A61B 2090/364* (2016.02); *A61B 2090/365* (2016.02); *A61B 2090/374* (2016.02); *A61B 2090/376* (2016.02); *A61B 2090/378* (2016.02); *A61B 2090/3762* (2016.02); *G06T 2207/10072* (2013.01); *G06T 2207/10081* (2013.01); *G06T 2207/10104* (2013.01); *G06T 2207/10108* (2013.01); *G06T 2207/10116* (2013.01); *G06T 2207/20012* (2013.01); *G06T 2207/20182* (2013.01);
(Continued)

(58) Field of Classification Search
None
See application file for complete search history.

(56) References Cited

U.S. PATENT DOCUMENTS 9,589,374 B1 * 3/2017 Gao ...................... G06T 11/008
2008/0232667 A1   9/2008 Kitamura et al.
(Continued)

OTHER PUBLICATIONS

German Office Action for related German Application No. 10 2016 221 220.6 dated Jul. 4, 2017.

*Primary Examiner* — Tahmina N Ansari
(74) *Attorney, Agent, or Firm* — Lempia Summerfield Katz LLC

(57) ABSTRACT

A method is provided for establishing an overlay image to be displayed from medical image datasets of a recording region of a patient registered with one another containing at least two items of different image information. The method includes establishing, for at least a part of the overlay image, an image value of the overlay image at an image position by addition or subtraction of an image value of at least one base image dataset of the medical image datasets at the image position and a modified image value of at least one modification image dataset of the medical image datasets at the image position dependent on the image value of the base image dataset at the image position.

17 Claims, 2 Drawing Sheets

16 Base image dataset
17 Overlay image
18 Modification image dataset
19 Combine datasets
20 Modify combined image
21 Dependency of image values
f  Linear weighting function

(51) Int. Cl.
*G06T 5/20* (2006.01)
*G06T 7/00* (2017.01)
(52) U.S. Cl.
CPC ............... *G06T 2207/20221* (2013.01); *G06T 2207/20224* (2013.01); *G06T 2207/30101* (2013.01)

(56) References Cited

U.S. PATENT DOCUMENTS

| | | |
|---|---|---|
| 2011/0142318 A1 | 6/2011 | Chen et al. |
| 2013/0038629 A1* | 2/2013 | Lautenschlager ..... G06F 19/321 345/629 |
| 2013/0211238 A1* | 8/2013 | DeCharms ........... A61B 5/4824 600/418 |
| 2014/0187942 A1 | 7/2014 | Wang et al. |
| 2016/0012592 A1 | 1/2016 | Chou et al. |
| 2016/0080665 A1 | 3/2016 | Barnes et al. |
| 2016/0117823 A1 | 4/2016 | Isaacs et al. |
| 2016/0247325 A1* | 8/2016 | Yu ........................ G16H 30/20 |
| 2018/0122088 A1* | 5/2018 | Ertel ..................... A61B 34/20 |

* cited by examiner

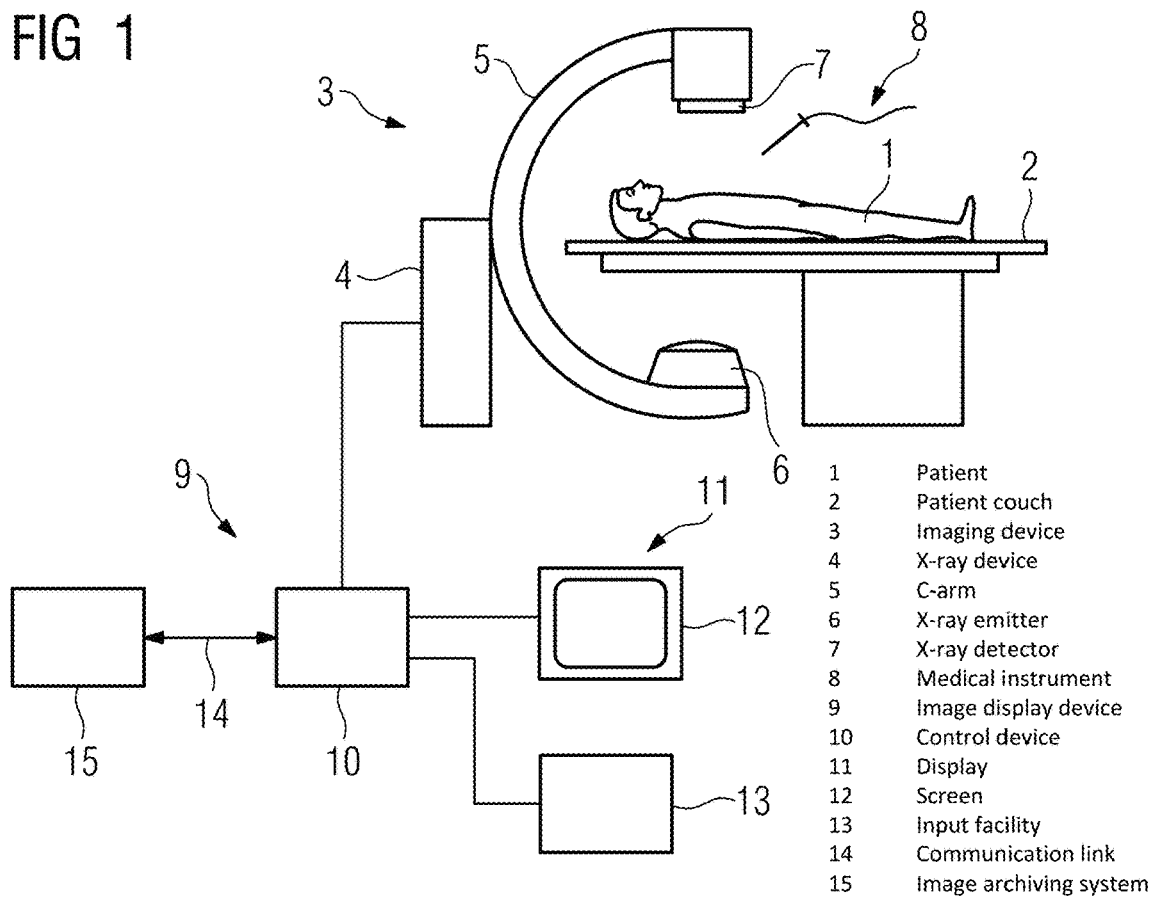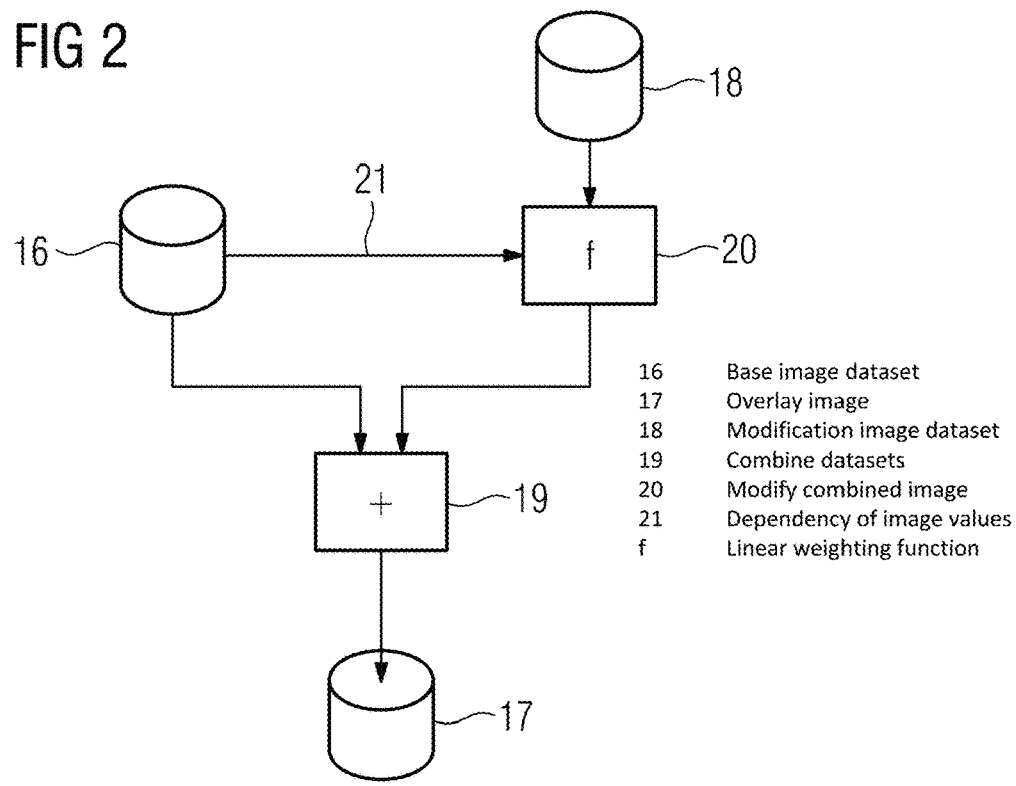

| 20 | Modify combined image |
| 22 | Threshold value analysis |
| 23 | Apply linear weighting function |
| 24 | Image value remains unchanged |

| 8 | Modify combined image |
| 25 | Threshold value analysis |
| 26 | Apply linear weighting function |
| 27 | Image value remains unchanged |
| 28 | Portions of instrument that appear outside blood vessel |

…

ESTABLISHING AN OVERLAY IMAGE TO BE DISPLAYED FROM A BASE IMAGE DATASET AND A MODIFICATION IMAGE DATASET OF MEDICAL IMAGE DATASETS

The application claims the benefit of German Patent Application No. DE 10 2016 221 220.6, filed Oct. 27, 2016, incorporated by reference in its entirety.

TECHNICAL FIELD

The disclosure relates to a method for establishing an overlay image to be displayed from medical image datasets of a recording region of a patient registered with one another containing at least two different items of image information. In addition, the disclosure relates to a display device, to a computer program, and to an electronically-readable data medium.

BACKGROUND

For a plurality of medical applications, (e.g., in medical diagnostics or in medical therapy), the use of a great diversity of imaging modalities is widely known. In these applications, such diagnostics or such a therapy may be undertaken in many cases using a single medical image dataset, e.g., a single computed tomography (CT) image dataset or a magnetic resonance (MR) image dataset.

Most notably with more complex problems, but also within the framework of the monitoring of medical interventions, the use of a number of image sources, thus medical image datasets, is frequently required, for example, a CT image dataset and a Positron Emission Tomography (PET) image dataset. Such different medical image datasets represent different image information, in the example of the CT image dataset anatomical structures, in the example of the PET image dataset the metabolism and/or functional information. A significant added value compared to a separate display of these independent medical image datasets is obtained in an overlaid presentation of the medical image datasets as an overlay image. For example, the medical image datasets may be registered with one another and subsequently displayed overlaid, so that a spatial correspondence of the different sources of information is created. An overlay image thus makes it possible for a user immediately to grasp the different items of image information together.

The display of a number of items of image information from different image sources in a single overlay image leads to further challenges and even to restrictions. One problem that arises will be explained below using the example of a roadmap procedure in an angiographic intervention. In this case two independent medical image datasets of Digital Subtraction Angiography (DSA) may be displayed overlaid, namely on the one hand a first medical image dataset, which has been recorded with the application of contrast media, so that only the blood vessel tree is presented, as a second medical image dataset a current live subtraction image without application of contrast medium, which shows an instrument, (e.g., a guide wire), used within the framework of the minimally-invasive intervention.

The result of displaying the vessels in the first medical image dataset here may be extremely high intensity values of the display, e.g., by the overlaying of a number of blood vessels. There is thus a very high image value present in such regions, so that a bright display is produced. Individual vessels are not clearly shown here, so this may already result in sharp differences in contrast within the displayed blood vessel system. The second medical image dataset dependent thereon, the live subtraction image, which shows the instrument, is characterized by a constant level of contrast however, which means that the instrument, (e.g., a guide wire), is displayed consistently over its entire length. If these two medical image datasets are now overlaid, the instrument may be only recognized with great difficulty in very bright vessel regions, which may lead to a misinterpretation of the overlay image. Similar problems also arise in other application areas, for example, if one of the medical image datasets exploits the available intensity dynamics of the display to the maximum for example and thus the result may display problems at specific contrasts of the other medical image dataset.

SUMMARY AND DESCRIPTION

The scope of the present disclosure is defined solely by the appended claims and is not affected to any degree by the statements within this summary. The present embodiments may obviate one or more of the drawbacks or limitations in the related art.

The underlying object of the disclosure is to specify a possibility for improving the recognizability of the image information of all image sources in an overlay image.

To achieve this object, in a method of the type stated above, there is provision at least for a part of the overlay image, for an image value of the overlay image at an image position to be established by addition or subtraction of an image value of at least one base image dataset of the medical image datasets at the image position and a modified image value of at least one modification image dataset of the medical image datasets at the image position dependent on the image value of the base image dataset at the image position.

In this case, the dimensionality of the image datasets described here plays only a minor role, because methods are known for establishing an image value in the image space of an overlay image even with high-dimensional image datasets, (e.g., projections, render algorithms, and the like). Image positions in such cases include in particular pixels, if the overlay image is to be two-dimensional; for high-dimensional overlay images, voxels may naturally also be considered as image positions (e.g., picture elements).

In accordance with the disclosure, it is thus proposed for at least one of the medical image datasets to undertake a modification of the image value when establishing the overlay image as a function of the corresponding image value of at least one other of the medical image datasets. The modification serves to improve the visibility of the image information of the modification image dataset in the overlay image, meaning that the image value of the modification image dataset is modified to enhance the contrast between the image information of the modification image dataset and of the base image dataset. In other words, the method offers an opportunity for local signal adaptation within an overlay image from independent image sources, by which the signal strength of at least one of the medical image datasets to be overlaid is raised or attenuated in its form, so that a sufficient recognizability of the image information may be guaranteed. An interaction between a user and the display device is reduced.

In such cases, the signal adaptation, (e.g., the modification of the image value of the modification image dataset), relates to a base image dataset of which the image values are not currently to be modified. A manipulation of image sources, which may lead to a misinterpretation, is intended to be prevented in this way. In this context, an expedient embodiment makes provision for the at least one base image dataset to be selected as a medical image dataset having anatomical features, which are to be recognizable unchanged in the overlay image. If, for example, the image support for a minimally-invasive intervention into the blood vessel system of a patient is considered, a medical image dataset showing the vessel system is expediently included as the base image dataset. In this case, there may not be a signal adaptation in the display of the blood vessel system, so that characteristic features of the vessel system continue to be recognizable, for example, the overlaying of a number of blood vessels. If, in another example, an overlay display of PET and CT image datasets is employed, the computed tomography image may remain unchanged as the base image dataset, because a modification of the image values of the CT image dataset would necessarily damage the required Hounsfield Units (HU) normalization.

Expediently, a medical image dataset in which a modification of the image values does not have to lead to a loss of significant image information is thus selected as the modification image dataset. For example, there may be provision for the modification image dataset to be selected as a medical image dataset containing a medical instrument and/or functional data. For a medical instrument, for example, as part of the image support during a minimally-invasive intervention, the current position/location of the medical instrument is decisive, so that where necessary different renderings or contrast transitions within the medical instrument are less critical, because the inner structure of the medical instrument does not involve information that is relevant for the user. As regards functional data, for example, as part of functional magnetic resonance imaging, this is frequently color-coded, so that the actual intensity, to which the modification may be limited, which will be discussed in greater depth below, is not itself an information carrier.

If the modification is described as a multiplicative weighting function f, I refers to image values and furthermore the indices "Display" refer to the overlay image, "Base" to the base image dataset and "Overlay" to the modification image dataset, the method may be written for each image position (x, y) as:

$$I_{display}(x,y) = I_{base}(x,y) + (I_{overlay}(x,y) \cdot f(I_{base}(x,y))).$$

Thus, there is a weighting of the modification image dataset $I_{overlay}(x,y)$ as a function of the base image dataset $I_{base}(x,y)$ locally. This involves a specific signal weighting for each individual image position, here of each individual pixel (x,y).

In order to obtain the different image information of the medical image datasets, there may be provision for at least some of the medical image datasets to be recorded with different imaging modalities and/or different imaging methods. Possible imaging modalities for medical imaging applications are, for example, magnetic resonance (MR) imaging, X-ray imaging, positron emission tomography (PET) imaging, single-photon emission computed tomography (SPECT) imaging, and ultrasound imaging. Different imaging methods exist for these imaging modalities, which in some cases are also able to be used in combination. Examples for imaging methods that may be usefully employed within the framework are digital subtraction angiography, computed tomography, functional imaging, and the like.

In an especially advantageous embodiment, there is provision for the overlay image to be established and displayed as an accompaniment to a minimally-invasive intervention at a patient, wherein the base image dataset shows the anatomy in the intervention region and the modification image dataset shows a minimally-invasive instrument used in the intervention. In other words, a method for image support during a minimally-invasive intervention at a patient is then provided, in which an overlay image to be displayed is established from at least two medical image datasets of a recording region of a patient, (e.g., the intervention region), containing different image information, registered with one another, wherein for at least a part of the overlay image an image value of the overlay image at an image position is established by addition or subtraction of an image value of at least one base image dataset of the medical image datasets at the image position showing the anatomy in the intervention region and a modified image value depending on the image value of the base image dataset at the image position of at least one modification image dataset of the medical image datasets at the image position showing a minimally-invasive instrument used during the intervention. The minimally-invasive intervention may involve an intervention into a blood vessel system of the patient in an angiography laboratory. X-ray devices with a C-arm are used as imaging devices there, for example, wherein an imaging device of this type may also be used to record the medical image datasets. The base image dataset may show the blood vessel system of the patient, while the modification image dataset obtained by fluoroscopic images for example shows the medical instrument. In particular, the method is able to be used to advantage for what is known as a "roadmap procedure".

In an expedient embodiment, there may be provision that, for modification of the image value of the modification image dataset, this is multiplied by a linear or non-linear weighting function of the image value of the base image dataset depending on the image value of the base image dataset at the corresponding image position. The dependence on the image value of the base image dataset at the image position may thus be described, for example, by a linear or a non-linear function, so that thus a weighting of the image value of the modification image with the function value of the function takes place. A linear function may be written, for example, as $f(I_{base}(x,y)) = k \cdot I_{base}(x,y)$ with a specific weighting parameter k, which is in particular selected so that an amplification takes place. The linear weighting function may amplify the image value of the modification image dataset in regions of high image values of the base image dataset.

Another embodiment makes provision for an exponential function and/or a saturation function to be used as the non-linear weighting function. In particular, exponential functions in such cases adhere to the x-ray law and are able to be employed especially usefully for medical image datasets based on X-rays as the imaging modality. In particular, saturation curves tuned to a presentation device being used, (e.g., a display), may map the available dynamics and thus implicitly insure a sufficient contrast of the different image information. An example for an exponential function is for example given by:

$$f(I_{base}(x,y)) := k_1 \cdot (1 + e^{-k_2(I_{base}(x,y) - k_3)})^{-1},$$

wherein $k_i$ are specific weighting parameters.

In addition, or as an alternative, an expedient development makes provision for the function to be the application of a filter acting locally of the respective image value of the base image dataset, based on a priori knowledge about the image information of the base image dataset, in particular a lowpass filter. Such a filter may also be described by a filter function. Such a filter may naturally also be supplemented by other filters, for example, noise reduction filters. Expediently there may also be provision for the a priori knowledge (and thus the concrete embodiment of the local effect of the filter) to be obtained by an evaluation of the base image dataset.

A concrete embodiment makes provision, in a base image dataset showing the blood vessel system as image information, for the course of the blood vessels and/or a direction of the blood vessels and/or a number of overlapping blood vessels per image position to be established as a priori knowledge, wherein there is lowpass filtering by the filter in particular outside blood vessels. For example, computed tomography image datasets of a blood vessel system established by digital subtraction angiography are mostly characterized by exhibiting only little noise for the image information, in particular, no relevant noise in the region of brightly displayed blood vessels. It may thus be expedient to apply a lowpass filter outside blood vessels in order to compensate for unwanted noise amplification effects and the like. The location of the blood vessels in such cases may be undertaken as part of the image evaluation of the base image dataset described and accordingly be included in the filter. Thus, a priori knowledge is obtained from the base image dataset, in order to apply a filter specifically adapted locally as a result of this a priori knowledge to the base image dataset, wherein the filter result as a function value determines the actual weighting.

Generally known image processing tools and image processing algorithms for evaluating the base image dataset may be used for establishing the a priori knowledge, for example, edge detection algorithms and/or threshold analyses and/or object recognition algorithms and/or morphological operators, (e.g., dilatation operators), and the like.

In an expedient development, there is provision for the dynamic range for the image value of the base image dataset to be divided into intervals and for it to be determined within which interval the image value of the base image dataset lies, wherein a modification action assigned to the interval is carried out from a group including no modification of the image value of the modification image dataset and/or at least one predetermined modification of the image value of the modification image dataset. In this manner in particular a type of threshold analysis of the base image dataset may be carried out. For example, there may be provision that only if the image value of the base image dataset lies in a specific range of values, (e.g., intervals), does a modification of the image value of the modification image dataset take place. If the image value of the base image dataset lies outside the interval, there may be provision, for example, for no modification of the image value of the modification image dataset to take place, which means that, for such an image position, the image value of the overlay image is established by addition or subtraction of the (e.g., unchanged) image values of the base image dataset and of the modification image dataset. For an image value of the base image dataset lying outside the interval, there may further be provision for there to be no overlay at all at this image position, in particular, thus for only the base image dataset to be displayed, which may be achieved algorithmically by the image value of the modification image dataset being hidden by multiplying it by zero. It is also conceivable for an image value of the base image dataset lying outside the interval to carry out a different type of modification than that for image values of the base image dataset lying inside the interval, for example, by employing an alternate function or alternate modification parameter for weighting. What has been said may of course also be transferred to the use of more than two intervals. In such cases, if a weighting function is used, the threshold value analysis or interval analysis used here may also be integrated into the execution of this weighting function.

In particular, if a linear weighting function and/or a weighting function that produces zero zero for an image value of the base image dataset is used, it is advantageous for there only to be a modification of the image value of the modification image dataset if a threshold value is exceeded by an image value of the base image dataset. For example, for image support during a minimally-invasive intervention, in which a medical instrument displayed by the modification image dataset is moved through a blood vessel system shown in the base image dataset, it may occur that correct spatial correspondence between the instrument and the blood vessels does not arise, thus in the image for example a guide wire does not completely overlap with the blood vessels, but runs partly outside the vessel. This means that only an extremely low signal strength of the base image dataset is present outside the vessel, (e.g., a low image value), which may lead to a disproportionate attenuation in this region, so that the signal or the image information of the instrument may be suppressed. However, it is possible, by the threshold value analysis described, to suppress the modification outside vessels, for example, so that just such an undesired attenuation will be avoided. Naturally, this type of approach may also be applied in all other cases of overlays, in which parts of the base image dataset are present with a dark background and parts are present with a light background, on which bright objects of the modification image dataset are to be displayed.

In an embodiment of the method, there may further be provision for the modification to be done as a function of at least one modification parameter able to be set by the user. Thus, the method will be expanded such that a user may influence the signal adaptation, e.g., the signal strength. To do this, at least one modification parameter is introduced, which may be applied within the weighting function, for example. The modification parameters may be selected in such cases so that they influence the image effect globally. When a linear weighting function is used, for example, a weighting parameter describing the gradient may be used as the modification parameter; also with the example given above for an exponential function the corresponding weighting parameters $k_i$ may be used as modification parameters or may be established by a function of the at least one modification parameter. Also, filter parameters within a filter function, (e.g., the cut-off sequence of a lowpass filter), may be adapted under user control as or via a modification parameter.

In this way, the user thus has the opportunity of directly influencing the overlay display, for example, through the operation of an assigned control element, in particular, a joystick. The image impression may be set to their requirements. This development of the method makes it possible for the user, for example, to increase the global contrast of the display of a medical instrument during image support of a minimally-invasive intervention.

In this context, an expedient development makes provision for the ability to set the modification parameters able to be set by the user to be restricted to a range of values increasing the contrast between image information of the medical image datasets. Thus, the ability to make settings is restricted, so that only "sensible" values of the modification parameters are possible, which also actually allow an improvement in the visibility of the individual image information.

It is further expedient if, for a colored modification image dataset, the modification acts on the display intensity, but not on the color coding. The present disclosure cannot just be applied to an overlay display of black/white image datasets, (e.g., of X-ray images), but also to overlay displays, which, in particular in the form of the modification image dataset, contain color-coded information, for example, PET image datasets. If the modification of the image values is applied to the color-coded medical image dataset, it is expedient for the presented modification of the image values during the establishment of the overlay image to be applied merely to the intensity of the corresponding display and for the color coding itself to remain uninfluenced. For example, the overlay image may thus be created by combination of the base image dataset and the signal-weighted combination image dataset weighted with the image values of the base image dataset via a corresponding weighting function. Thus, the characteristic of the color coding is explicitly retained in the signal weighting, so that information contained in the color coding is not lost. In many cases, color-coded medical image datasets and tomographic medical datasets are to be overlaid, wherein the application of the modification to the color-coded medical image dataset as modification image dataset is also advantageous for the reason that the required signal normalization of the tomographic medical image datasets as base image datasets continues to be guaranteed, for example, the HU normalization of computed tomography images.

It is also conceivable to make modifications to specific colors, e.g., to provide specific weighting functions for red components, green components, and blue components, if this does not distort image information contained in the modification image dataset or make it incomprehensible in the overlay image.

As well as the method, the present disclosure also relates to a display device, having a display, (e.g., a screen), and a control device embodied for carrying out the method. Everything that has been said in relation to the method is able to be transferred by analogy to the display device. The display device may include an image support facility for a minimally-invasive medical intervention and/or an overlay image establishment unit with a corresponding modification unit.

A computer program is able to be loaded for example directly into a memory of a control device of a display device or into another computing device and has program code for carrying out the acts of a method when the computer program is executed in the computing device. The computer program may be stored on an electronically-readable data medium, which thus includes electronically-readable control information stored thereon, which includes at least a said computer program and which is embodied such that, when the data medium is used in a computing device, it carries out a method described in this document. The data medium may involve a non-transient data medium, for example a CD-ROM.

BRIEF DESCRIPTION OF THE DRAWINGS

Further advantages and details of the present disclosure emerge from the exemplary embodiments described below and also with reference to the drawings, in which:

FIG. 1 depicts an example of a system including a display device.

FIG. 2 depicts an example of a diagram for explaining the method.

DETAILED DESCRIPTION

Figure 3:
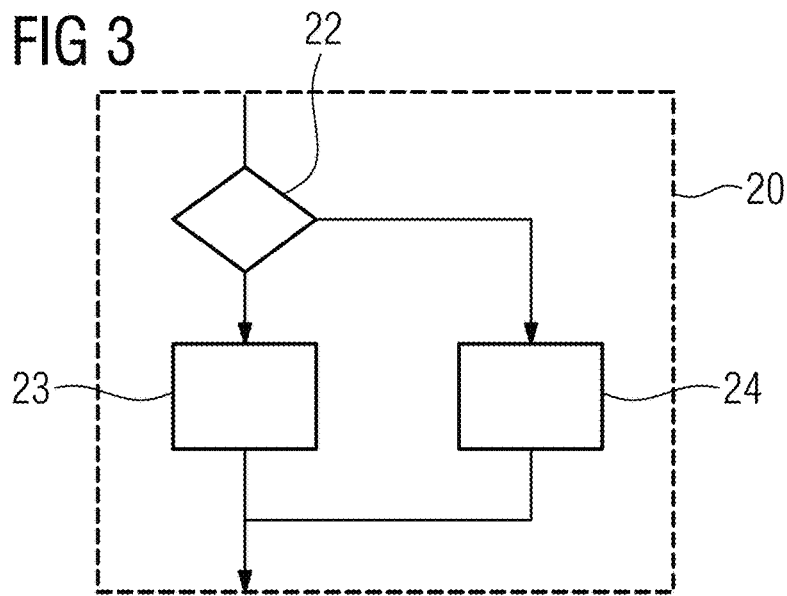
FIG. 3 depicts an embodiment of the modification act.

The method is to be presented below in an application for image support during a minimally-invasive intervention in a blood vessel system of a patient, in particular, a roadmap procedure. This application is to be understood as an example; the process may also be used above and beyond this in diverse ways, whenever overlay images are to be viewed in a medical context.

FIG. 1 depicts a system in which the medical intervention and also the image monitoring may be carried out. The patient 1 to be treated or to be examined is supported in this case on a patient couch 2. Image data of the patient 1 may be recorded with an imaging device 3, here an X-ray device 4 with a C-arm 5, on which an X-ray emitter 6 and an X-ray detector 7 are arranged opposite one another. The minimally-invasive intervention itself is carried out with at least one medical instrument 8, for example, a guide wire and/or a catheter.

For planning of the minimally-invasive intervention here the X-ray device 4 (or a dedicated computed-tomography device) is used, in order to establish, by digital subtraction angiography with administration of contrast medium, a three-dimensional medical image dataset of the blood vessel system of the patient 1 in which the medical instrument 8 is to be moved. During the minimally-invasive medical intervention, fluoroscopic X-ray images are repeatedly recorded at a low dose with the x-ray device 4 in order to be able to follow the position of the medical instrument 8 within the patient 1. These X-ray images then mostly show as usable image information only the medical instrument 8, which stands out clearly, even at a low dose. Each of these X-ray images now forms a further medical image dataset.

The registration of the medical image dataset showing the blood vessel system and the X-ray images is already known in the prior art, in order to enable an overlay image of the two medical image datasets to be created, in which the image information of both medical image datasets is to be detectable simultaneously for an observer, in particular the position of the medical instrument 8 in the blood vessel system of the patient 1 is visible. The establishment and display of the overlay image is done in the present example in an image display device 9, which is embodied here as an image support device and in addition to a control device 10, which is embodied for carrying out the method, also has a screen 12 as a display 11. The image display device 9 further includes an input facility 13, including for example an operator console, a keyboard, and/or a mouse. The screen 12 and the input facility 13 may be accessible for example at a mobile operator console in the intervention area.

In the present example, the image display device 9 also has a communication link 14 to an image archiving system 15 (e.g., PACS), in order also to be able to include further medical image datasets for establishing overlay images.

The establishment of the overlay image is carried out by the control device 10 in a manner that obtains the relevant image information of both image datasets and arranges it for improved recognition within the overlay image. This process is explained in greater detail by the basic diagram depicted in FIG. 2. In this process, it is first to be determined that, in relation to the first medical image dataset showing the blood vessel system of the patient 1, a modification of the signal intensities, (e.g., of the image values), is not desired, because otherwise the anatomy shown in the image dataset would no longer able to be recognized well enough, for example, as regards overlays of blood vessels and the like. The first medical image dataset showing the blood vessel system of the patient 1 is thus determined in the present example as the base image dataset 16, of which the image values are to be included unchanged in the overlay image 17. By contrast, the second medical image dataset, the current fluoroscopic X-ray image, reproduces as its image information the position of the medical instrument 8, in which it is important to be able to easily recognize the location of the instrument 8, while signal variations, thus image value fluctuations, within the display of the instrument 8 itself are less relevant. In the present example, the second medical image dataset, which shows the instrument 8, thus forms a modification image dataset 18 to be modified. Before the image values of the base image dataset 16 and of the modification image dataset 18 are combined in act 19 by addition or subtraction for the individual image positions, here pixels of the overlay image, the image values of the combination image dataset 18 are modified in act 20 depending on the image values of the base image dataset 16 at the image position currently considered, wherein the dependency on the image values of the base image dataset 16 is illustrated by the arrow 21.

In the present example, the modification in act 20 is undertaken by using a linear weighting function f dependent on the image value of the base image dataset 16 at the image position of the overlay image 17 currently considered, wherein the weighting parameter describing the gradient of the linear weighting function as modification parameter is able to be adapted in the present example by a user by an operating element at the input facility 13, but restricted to a sensible range of values, in which the weighting function may then also actually lead to an increase of the contrast between the image information of the medical image datasets 16, 18. The use of a linear function as weighting function f is to be understood as an example; naturally other, in particular non-linear weighting functions f may be used, for example an exponential function or a filter function, wherein the filter effect is adapted depending on a priori knowledge, which was obtained by evaluation of the base image dataset 16. Different weighting functions may also be employed cumulatively, wherein it is expedient in the present concrete exemplary embodiment, to use both the linear weighting function and also a filter function, which realizes a lowpass filter, which is applied outside blood vessels (of which the course has been determined through the evaluation as a priori knowledge), in order to reduce the noise.

FIG. 3 illustrates an option for actual implementation of act 20. The sub-acts shown may be integrated into the weighting function f, but may also be realized as an additional module outside this function. In this case, in a sub-act 22, first of all a threshold value analysis is carried out. The threshold value, against which the image value of the base image dataset 16 is checked, is selected in this case so that a distinction may be made between regions within blood vessels and outside blood vessels. Thus, the blood vessels and the regions outside blood vessels are assigned intervals of the possible intensities. Only when it is established in act 22 that the image value of the base image dataset at the image position currently process exceeds the threshold value will the linear weighting function be applied in a sub-act 23. Otherwise, in a sub-act 24 the image value of the modification image dataset 18 remains unchanged. In this way, a signal suppression for the instrument outside blood vessels because of the low image values of the base image dataset 16 is avoided. In sub-act 24, as an alternative, other weighting functions may also be used, or the modification image dataset 18 may be hidden by setting the image value to zero. It is also conceivable, in particular in other application cases, to consider more than two intervals, to which modification actions are assigned in each case, in sub-act 22.

Figure 4:
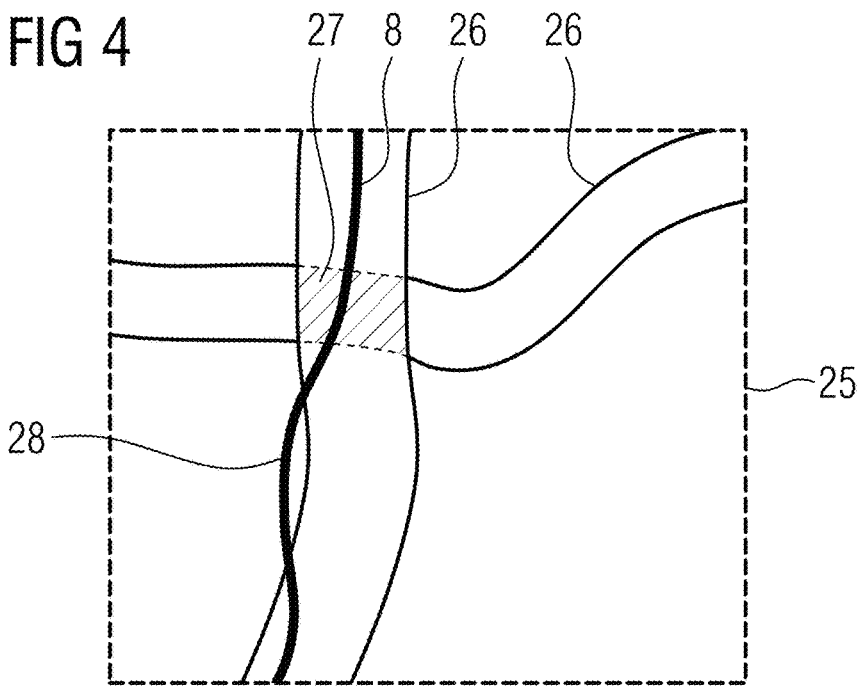
FIG. 4 depicts a section from an exemplary overlay image.

The modification actions and specifically the weighting functions, in act 20, may be selected in such cases so that the recognizability of the image information of both medical image datasets 16, 18 is improved and the corresponding image information is given sufficient contrast in the overlay image 17. For a more detailed explanation, FIG. 4 depicts a section 25 of an overlay image 17. Blood vessels 26 of the blood vessel system may be seen, which overlap in a region 27, so that an especially high signal value is produced there. This high signal value may lead, with an unmodified combination of the medical image datasets 16, 18, to the image value of the modification image dataset 18, which actually does contain information about the instrument 8, being "submerged" so to speak; the instrument 8 would be difficult or impossible to recognize. The modification in act 20 insures a sufficiently clear recognizability, as is also depicted in FIG. 4.

As was also explained in relation to FIG. 3, the exemplary embodiment presented here also addresses the problem of portions 28 of the instrument 8 that appear to lie outside blood vessels 26. These too remain easy to recognize, because the linear weighting function is not used here with the low image values of the base image dataset 16, which would have had a suppressing effect.

Finally, exemplary embodiments of the method, (e.g., for the overlaying of CT image datasets and PET image datasets), may also relate to color-coded medical image datasets, in which only the overall intensity may be modified for a color-coded modification image dataset 18, in order not to influence the color coding.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:
1. A method for establishing an overlay image to be displayed from medical image datasets of a recording region of a patient registered with one another containing at least two items of different image information, the method comprising:
  selecting, by a control device of an image display device, a base image dataset from the medical image datasets, wherein the base image dataset comprises anatomical features of the patient configured to be recognized unchanged in the overlay image;

selecting, by the control device, a modification image dataset from the medical image datasets, wherein the modification image dataset comprises a medical instrument, functional data, or both the medical instrument and the functional data;

establishing, by the control device, the overlay image from the base image dataset and the modification image dataset, wherein, for at least a part of the overlay image, an image value of the overlay image is calculated at an image position by adding or subtracting an image value of the base image dataset of the medical image datasets at the image position with a modified image value of the modification image dataset of the medical image datasets at the image position, wherein the modified image value is a function of the image value of the base image dataset at the image position; and displaying, by a display of the image display device, the overlay image.

2. The method of claim 1, wherein at least some of the medical image datasets are recorded with different imaging modalities, different imaging methods, or both different imaging modalities and different imaging methods.

3. The method of claim 1, wherein the overlay image is displayed as an accompaniment to a minimally-invasive intervention at a patient, and wherein the base image dataset shows an anatomy in an intervention region, and a combination image dataset shows a minimally-invasive instrument used in the intervention.

4. The method of claim 1, wherein, for modification of the image value of the modification image dataset, the modification image dataset is multiplied by at least one linear or non-linear weighting function of the image value of the base image dataset at a corresponding image position dependent on the image value of the base image dataset.

5. The method of claim 4, wherein the linear weighting function, at least in regions of high image values of the base image dataset, amplifies the image value of the modification image dataset, uses an exponential function as the non-linear weighting function, uses a saturation function as the non-linear weighting function, or a combination thereof.

6. The method of claim 4, wherein the linear or non-linear weighting function is an application of a filter acting locally on the respective image value of the base image dataset, based on a priori knowledge about the image information of the base image dataset.

7. The method of claim 6, wherein the filter is a lowpass filter.

8. The method of claim 6, wherein the a priori knowledge is obtained by an evaluation of the base image dataset.

9. The method of claim 8, wherein, the base image dataset depicts a blood vessel system as the image information, and wherein a course of the blood vessels, a direction of the blood vessels, a number of overlapping blood vessels per image position, or a combination thereof is established as the a priori knowledge.

10. The method of claim 9, wherein lowpass filtering outside blood vessels is undertaken by the filter.

11. The method of claim 1, further comprising:

subdividing a dynamic range for the image value of the base image dataset into intervals;

establishing which interval the image value of the base image dataset lies; and assigning a modification action to the interval from a group comprising no modification of the image value of the modification image dataset, and/or carrying out at least one predefined modification of the image value of the modification image dataset.

12. The method of claim 11, wherein, when a linear weighting function and/or a weighting function produced for an image value of the base image dataset of zero zero is used, there is only a modification of the image value of the modification image dataset when a threshold value is exceeded by the image value of the base image dataset.

13. The method of claim 1, wherein the modification is made as a function of at least one modification parameter able to be set by a user.

14. The method of claim 13, wherein the modification parameter able to be set by the user is restricted to a range of values increasing the contrast between image information of the medical image datasets.

15. The method of claim 1, wherein, with a colored modification image dataset, the modification acts on a display intensity, but not on the color coding.

16. A display device comprising:
a display; and
a control device configured to:
    select a base image dataset from medical image datasets, wherein the base image dataset comprises anatomical features of a patient configured to be recognized unchanged in an overlay image;
    select a modification image dataset from the medical image datasets, wherein the modification image dataset comprises a medical instrument, functional data, or both the medical instrument and the functional data;
    establish the overlay image from the base image dataset and the modification image dataset, wherein, for at least a part of the overlay image, an image value of the overlay image is calculated at an image position by adding or subtracting an image value of the base image dataset of the medical image datasets at an image position with a modified image value of the modification image dataset of the medical image datasets at the image position, wherein the modified image value is a function of the image value of the base image dataset at the image position; and
    display the overlay image.

17. A non-transitory electronically-readable data medium, on which a computer program is stored, wherein the computer program is configured to cause a control device to:
    select a base image dataset from medical image datasets, wherein the base image dataset comprises anatomical features of a patient configured to be recognized unchanged in an overlay image;
    select a modification image dataset from the medical image datasets, wherein the modification image dataset comprises a medical instrument, functional data, or both the medical instrument and the functional data;
    establish the overlay image from the base image dataset and the modification image dataset, wherein, for at least a part of the overlay image, an image value of the overlay image is calculated at an image position by adding or subtracting an image value of the base image dataset of the medical image datasets at an image position with a modified image value of the modification image dataset of the medical image datasets at the image position, wherein the modified image value is a function of the image value of the base image dataset at the image position; and
    display the overlay image.

* * * * *